United States Patent
Buysch et al.

(10) Patent No.: US 6,548,445 B1
(45) Date of Patent: *Apr. 15, 2003

(54) SUPPORTED CATALYSTS CONTAINING A PLATINUM METAL AND PROCESS FOR PREPARING DIARYL CARBONATES

(75) Inventors: Hans-Josef Buysch, Krefeld (DE); Carsten Hesse, Krefeld (DE); Jörg-Dietrich Jentsch, Mülheim (DE); Johann Rechner, Kempen (DE); Eberhard Zirngiebl, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/625,613

(22) Filed: Mar. 29, 1996

(30) Foreign Application Priority Data

Apr. 5, 1995 (DE) .......................... 195 12 615

(51) Int. Cl.$^7$ ........................... B01J 27/13; B01J 23/00; B01J 23/58; C07C 69/96
(52) U.S. Cl. .............. 502/230; 502/308; 502/309; 502/311; 502/318; 502/321; 502/324; 502/330; 502/345; 502/350; 502/353; 558/270; 558/271; 558/274; 558/275
(58) Field of Search .......................... 502/230, 308, 502/309, 311–316, 318, 321, 324–326, 330, 331, 345, 350, 353; 558/270, 274, 275, 271

(56) References Cited

U.S. PATENT DOCUMENTS

| | | | | |
|---|---|---|---|---|
| 4,039,572 A | * | 8/1977 | Funakoshi et al. | 260/468 K |
| 5,235,087 A | | 8/1993 | Klausener et al. | 558/260 |
| 5,473,094 A | * | 12/1995 | Ooms et al. | 558/270 |
| 5,498,742 A | * | 3/1996 | Buysch et al. | 558/274 |
| 5,498,744 A | * | 3/1996 | Jenisch et al. | 558/277 |
| 5,502,232 A | * | 3/1996 | Buysch et al. | 558/270 |
| 5,516,878 A | * | 5/1996 | Sasaki et al. | 502/150 |
| 5,527,875 A | * | 6/1996 | Yokoyama et al. | 528/196 |
| 5,527,942 A | * | 6/1996 | Ooms et al. | 558/274 |
| 6,001,768 A | * | 12/1999 | Buysch et al. | 502/230 |

FOREIGN PATENT DOCUMENTS

| | | | |
|---|---|---|---|
| DE | 2815512 | 10/1979 | C07C/69/96 |
| EP | 0464460 | 1/1992 | C07C/69/96 |
| EP | 0503581 | 9/1992 | C07C/68/00 |
| EP | 0572980 | 8/1993 | C07C/69/96 |
| EP | 0581240 | 2/1994 | C07C/68/00 |
| EP | 0607943 | 7/1994 | C07C/68/00 |
| EP | 0614876 | 9/1994 | C07C/68/00 |
| EP | 0654461 | 5/1995 | C07C/68/00 |
| GB | 1578713 | 11/1980 | C07C/68/00 |
| JP | 1165551 | 6/1989 | |
| JP | 4257546 | 9/1992 | C07C/69/96 |
| JP | 4261142 | 9/1992 | C07C/69/96 |

* cited by examiner

Primary Examiner—Mark L. Bell
Assistant Examiner—Patricia L. Hailey
(74) Attorney, Agent, or Firm—Norris McLaughlin & Marcus

(57) ABSTRACT

In the process for preparing an aromatic carbonate from an aromatic hydroxy compound, CO and $O_2$ in the presence of a quaternary salt and a base using a platinum metal catalyst and a cocatalyst, use is advantageously made of supported catalysts containing, in the reaction-ready state, (i) a platinum metal, a platinum metal halide or a platinum metal halide complex and (ii) a metal compound acting as cocatalyst from groups IB, IIB, IIIA, IIIB, IVA, IVB, VB, VIB, VIIB, the iron group (atomic numbers 26–28) or the rare earth metals (atomic numbers 58–71) of the Periodic Table of the Elements (Mendeleev), each in an amount of 0.01–15% by weight, calculated as metal and based on the total weight of the catalyst.

20 Claims, No Drawings

SUPPORTED CATALYSTS CONTAINING A PLATINUM METAL AND PROCESS FOR PREPARING DIARYL CARBONATES

BACKGROUND OF THE INVENTION

1. Field of the Invention

The present invention relates to supported catalysts containing a platinum metal and their use in processes for preparing diaryl carbonates by reaction of aromatic hydroxy compounds with carbon monoxide and oxygen, which are characterized in that the supported catalysts contain at least one cocatalyst in addition to the platinum metal.

2. Description of the Related Art

It is known that organic carbonates can be prepared by oxidative reaction of aromatic hydroxy compounds with carbon monoxide in the presence of a noble metal catalyst (German Offenlegungsschrift 28 15 512). The noble metal preferably used is palladium. In addition, a cocatalyst (e.g. manganese or cobalt salts), a base, a quaternary salt, various quinones or hydroquinones and desiccants can be used. The reaction can be carried out in a solvent, preferably methylene chloride.

For economically carrying out this process, not only the activity and the selectivity but also the effective recovery of the noble metal catalyst are of decisive importance: for one thing, the noble metal catalyst represents a considerable cost factor. Losses of noble metal catalyst have to be replaced at high cost. Furthermore, no residues of noble metal catalyst may remain in the product. For the process of oxidative carbonylation of aromatic hydroxy compounds to give diaryl carbonates, the economical and efficient recovery of homogeneous catalysts has hitherto not been described. A noble metal catalyst can be separated from a liquid reaction mixture with little effort, e.g. by filtration or centrifugation, if heterogeneous catalysts, e.g. supported catalysts, are used.

For preparing supported catalysts, suitable materials are known. Depending on the type of process, use is made of supports having a high internal surface area, for example aluminium oxide, magnesium oxide, activated carbon or silicon dioxide having more than 50 m$^2$ of surface area per gram, supports having surface areas around 5 m$^2$/g and correspondingly larger pore radii, for example carbon black, titanium dioxide, iron oxide or zinc oxide, or coarse-grained supports, for example silicon carbide and corundum (Ullmanns Enzyklopädie der technischen Chemie, 3rd edition, Berlin/Munich 1957, Volume 9, p. 263 ff). Essentially, it is possible to use both synthetic materials such as activated aluminium oxides, silica gels, silicates, titanium dioxides or activated carbons and also materials from natural sources, for example pumice, kaolin, bleaching earths, bauxites, bentonites, kieselguhr, asbestos or zeolites. In EP 572 980, EP 503 581 and EP 614 876, use is made of supported noble metal catalysts containing 5% of palladium on carbon supports. However, according to our own studies, such supported catalysts give only very unsatisfactory conversions, if any, so that these too are not suitable for an economical process. In JP 01/165 551 (cited according to C.A. 112 (1990), 76618j) it is stated that, for the preparation of aromatic carbonates, palladium or palladium compounds such as palladium acetylacetonate can be used in combination with alkali metal (alkaline earth metal) iodides or onium iodides such as tetrabutylammonium iodide and at least one zeolite. JP 04/257 546 and JP 04/261 142 describe, in one example each, a supported catalyst for preparing aromatic carbonates in which granulated silicon carbide is used as support material for a supported catalyst in a distillation column. Although the relevant examples are carried out under drastic conditions (high pressure, high temperature), this catalyst makes possible only very low space-time yields. These low space-time yields make economical preparation of aromatic carbonates using such supported catalysts impossible.

Up to now, there is therefore no supported catalyst available by means of which diaryl carbonates can be prepared economically and efficiently by reaction of an aromatic hydroxy compound with carbon monoxide and oxygen. It was therefore an object of the invention to find a supported catalyst having high activity and selectivity which allows the economically efficient preparation of diaryl carbonates by reaction of an aromatic hydroxy compound with carbon monoxide and oxygen.

SUMMARY OF THE INVENTION

It has now been found that the above disadvantages can be overcome if use is made of supported platinum metal catalysts which contain at least one cocatalyst in addition to the platinum metal. The catalysts comprising platinum metal and at least one cocatalyst on a support are used according to the invention as powders, pellets or binder-containing extrudates. Suitable binders are, for example, SiO$_2$, Al$_2$O$_3$ or clay minerals. The binder contents can be varied within a wide range, for example from 0.5 to 99.5% by weight, based on the total weight of the support.

The supported catalysts of the invention contain, in the reaction-ready state, (i) a platinum metal, a platinum metal halide or a complex containing a platinum metal halide, or a compound which can be converted under the reaction conditions into a platinum metal, a platinum metal halide or a complex containing a platinum metal halide, in an amount of 0.01–15% by weight, preferably 0.05–10% by weight, calculated as platinum metal and based on the total weight of the catalyst, and (ii) a metal compound acting as cocatalyst from groups IB, IIB, IIIA, IIIB, IVA, IVB, VB, VIB, VIIB, the iron group (atomic numbers 26–28) or the rare earth metals (atomic numbers 58–71) of the Periodic Table of the Elements (Mendeleev) in an amount of 0.01–15% by weight, preferably 0.05–10% by weight, calculated as metal and based on the total weight of the catalyst.

Such catalysts are in the form of heterogeneously catalytic systems and thus make it easier to separate the reaction product from the expensive platinum metal, its compounds and the cocatalyst.

The invention further provides a process for preparing an aromatic carbonate of the formula

R—O—CO—O—R                 (I), where

R is substituted or unsubstituted C$_6$–C$_{12}$-aryl, preferably substituted or unsubstituted phenyl, particularly preferably unsubstituted phenyl, by reaction of an aromatic hydroxy compound of the formula

R—O—H                 (II), where R is as defined above,
with carbon monoxide and oxygen in the presence of a quaternary ammonium or phosphonium salt and a base at from 30 to 200° C., preferably 30–150° C., particularly preferably from 40 to 120° C., and at a pressure of from 1 to 150 bar, preferably 2–50 bar, particularly preferably from 5 to 25 bar, which is characterized in that use is made of supported platinum metal catalysts which contain one or more cocatalysts of the above-described type and amount in addition to the platinum metal.

DETAILED DESCRIPTION OF THE INVENTION

For the example of the formation of diphenyl carbonate, the process of the invention can be represented in terms of formulae as follows:

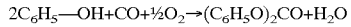

$$2C_6H_5\text{—OH} + CO + \tfrac{1}{2}O_2 \rightarrow (C_6H_5O)_2CO + H_2O$$

Catalyst supports suitable for use according to the invention are all industrially customary catalyst supports, for example those based on carbon, element oxides, element carbides or element salts in various use forms. Examples of carbon-containing supports are coke, graphite, carbon black or activated carbon. Examples of element oxide catalyst supports are $SiO_2$ (natural or synthetic silicas, quartz), $Al_2O_3$ ($\alpha$-, $\gamma$-$Al_2O_3$), aluminas, natural and synthetic aluminosilicates (zeolites), $TiO_2$ (rutile, anatase), $ZrO_2$ or $ZnO$. Examples of element carbides and salts are SiC, $AlPO_4$, $BaSO_4$, $CaCO_3$, etc. They can be used either as chemically uniform pure substances or in admixture. Catalyst supports suitable for use according to the invention can be either in the form of pieces or as pulverulent materials. If the supported catalyst is arranged in a fixed bed, the support is preferably used as shaped bodies, e.g. as spheres, cylinders, rods, hollow cylinders, rings, etc. If desired, catalyst supports can be further modified by extrusion, pelletizing, optionally with the mixing in of further catalyst supports or binders such as $SiO_2$ or $Al_2O_3$, and calcination. Preparation and further processing of the catalyst supports used according to the invention are well known to those skilled in the art and are prior art.

The reactive component of the catalyst comprises, in the reaction-ready state, a platinum metal, a platinum metal halide such as $PdCl_2$ or $PdBr_2$, or a complex containing a platinum metal halide, where the said complex can additionally contain, for example, olefins, amines, phosphines, nitriles, carbon monoxide or water, for example $A_2(PdHal_4)$, where A represents, for example, Li, Na, K, $NH_4$, Rb, Cs or $NR^1_4$ and $R^1$ represents an organic radical $C_6$–$C_{10}$-aryl, $C_7$–$C_{12}$-aralkyl and/or $C_1$–$C_{20}$-alkyl and Hal represents a halogen such as, for example, F, Cl, Br, I, and also at least one cocatalyst. Suitable platinum metal complexes are basically known. Examples are: $Li_2(PdCl_4)$, $Na_2(PdCl_4)$, $K_2(PdCl_4)$, $(NBu_4)_2(PdCl_4)$, $Na_2(PdBr_4)$, $K_2(PdBr_4)$, $(NBu_4)_2(PdBr_4)$ where Bu=n-butyl; examples of olefin-containing platinum metal complexes are [allylpalladium chloride] dimer—$[C_3H_5PdCl]_2$, 1,5-cyclooctadienepalladium dichloride—$C_8H_5PdCl_2$; examples of phosphine-containing platinum metal complexes are [1,2-bis(diphenylphosphino)ethane]palladium dichloride—$Pd[(C_6H_5)_2PCH_2CH_2P(C_6H_5)_2]Cl_2$, bis(triphenylphosphine)palladium dichloride—$Pd[P(C_6H_5)_3]_2Cl_2$; examples of amine-containing platinum metal complexes are diamminepalladium dibromide —$Pd(NH_3)_2Br_2$, diamminepalladium dichloride—$Pd(NH_3)_2Cl_2$, tetramminepalladium tetrachloropalladate—$[Pd(NH_3)_4][PdCl_4]$; examples of nitrile-containing platinum metal complexes are bis(acetonitrile)palladium dichloride—$Pd(CH_3CN)_2Cl_2$, bis(benzonitrile)palladium dichloride—$Pd(C_6H_5CN)_2Cl_2$; examples of carbon monoxide-containing platinum metal complexes are tetrabutylammonium tribromocarbonylpalladate—$(NBu_4)Pd(CO)Br_3$ (where Bu=n-butyl) and tetrabutylammonium trichlorocarbonylpalladate—$(NBu_4)Pd(CO)Cl_3$ (where Bu=n-butyl). In the examples mentioned, Pd has been specified as platinum metal, but other platinum metals are also suitable, for example Pt, Ir, Ru or Rh. However, Pd and Rh, in particular Pd, are preferred. The platinum metal is present in an oxidation state of from 0 to 4.

It has also been found that the platinum metal halide or the complex containing the platinum metal halide can be prepared in situ on the support during the preparation or during use of the catalyst under reaction conditions from a suitable halogen-free platinum metal compound and a halide-containing compound. Suitable halogen-free platinum metal compounds are, for example, platinum metal nitrates, acetates, propionates, butyrates, oxalates, carbonates, oxides, hydroxides, acetylacetonates and others with which those skilled in the art are familiar. Suitable halide-containing compounds are halogen-containing salts and complexes of the elements of the first to fifth main groups and the first to eighth transition groups of the Periodic Table of the Elements (Mendeleev) and also of the rare earth metals (atomic numbers 58–71), or aliphatic halogenated hydrocarbons. Examples are NaBr, NaCl, $MgCl_2$, $MgBr_2$, $AlCl_3$, $CH_2Cl_2$, $NaPF_6$, $MnCl_2$, $MnBr_2$, $CoBr_2$, $CeCl_3$, $SmI_2$, $CuCl_2$, $Na_2ZnCl_4$, $TiCl_4$ and $NR^1_4Br$, where $R^1$ is as defined above.

The amount of the platinum metal, platinum metal halide or of the complex containing the platinum metal halide in the reaction-ready state is from 0.01 to 15% by weight, preferably from 0.05 to 10% by weight, calculated as platinum metal and based on the total weight of the catalyst.

The cocatalyst used for the process of the invention is a metal compound of group I B, II B, III A, III B, IV A, IV B, V B, VI B, VII B, the iron group (atomic numbers 26–28) or the rare earth metals (atomic numbers 58–71) of the Periodic Table of the Elements (Mendeleev), preferably Mn, Cu, Co, V, Nb, W, Zn, Ce or Mo, particularly preferably Mn, Co, Cu, Mo or Ce. The metals can be used, for example, as halide, oxides, carboxylates of $C_2$–$C_6$-carboxylic acids, diketonates or nitrates and as complexes which can contain, for example, carbon monoxide, olefins, amines, nitriles, phosphines and halides.

The amount of compound containing the cocatalyst in the reaction-ready state is from 0.01 to 15% by weight, preferably from 0.05 to 10% by weight, calculated as metal and based on the total weight of the catalyst.

Platinum metal and cocatalyst can be applied to the support simultaneously, i.e. from a joint solution, or successively in any order. Suitable solvents for the platinum metal and cocatalyst compounds for preparing supported catalysts according to the invention are, for example, water, aliphatic hydrocarbons such as pentane, n-hexane, cyclohexane, etc., aliphatic halogenated hydrocarbons such as dichloromethane, trichloromethane, etc., unsaturated hydrocarbons such as pentene, isoprene, cyclopentadiene, hexenes, hexines, cyclohexenes, cyclooctadienes, etc., aromatic hydrocarbons such as benzene, toluene, xylene, etc., halogenated aromatic hydrocarbons such as chlorobenzene, dichlorobenzene, etc., primary, secondary or tertiary alcohols such as methanol, ethanol, n-propanol, iso-propanol, n-butanol, iso-butanol, t-butanol, cumyl alcohol, iso-amyl alcohol, diethylene glycol, etc., ketones such as acetone, 2-butanone, methyl isobutyl ketone, acetylacetone, etc., ethers such as diethyl ether, diisopropyl ether, methyl t-butyl ether, dioxane, tetrahydrofuran, etc., esters such as methyl acetate, ethyl acetate, etc., nitriles such as acetonitrile, benzonitrile, etc., carbonates such as dimethyl carbonate, diethyl carbonate, diphenyl carbonate, etc., amides such as dimethylacetamide, N-methylpyrrolidinone and tetramethylurea. Of course, mixtures of such solvents can also be used.

The catalysts to be used according to the invention are prepared by methods which are basically known to those skilled in the art. Thus, solutions of one or more of the platinum metal compounds specified and the halide-containing compounds specified and also one or more cocatalysts can be applied, for example by soaking, adsorption, dipping, spraying, impregnation and ion exchange, to the catalyst support to be used according to the invention. It is also possible to fix one or more platinum metals, the halide-containing compounds specified and also one or more cocatalysts on the support by precitation with a base. Suitable bases are, for example, alkali metal (alkaline earth metal) hydroxides such as $Ca(OH)_2$, $Mg(OH)_2$, NaOH, LiOH and KOH, alkali metal (alkaline earth metal) hydrogen carbonates such as $Ca(HCO_3)_2$, $Mg(HCO_3)_2$, $NaHCO_3$, $LiHCO_3$ and $KHCO_3$, alkali metal (alkaline earth metal) carbonates such as $CaCO_3$, $MgCO_3$, $Na_2CO_3$, $Li_2CO_3$ and $K_2CO_3$, alkali metal salts of weak organic acids, such as sodium acetate, potassium acetate and lithium acetate, and alkali metal (alkaline earth metal) salts of substituted or unsubstituted phenols (in the case of substituted phenols, these salts are those as are described further below as being usable in the process for preparing diaryl carbonate), such as lithium phenoxide, sodium phenoxide, sodium cresoxide and potassium phenoxide. The platinum metal and the halide-containing compound can be applied to the support either successively in any order or simultaneously. A specific embodiment of the invention comprises the application of the platinum metal by precipitation of a platinum metal halide or a platinum metal halide complex with a suitable base (suitable bases are, for example, those as are described above), reduction of the precipitated platinum metal base to the metal using a suitable reducing agent such as, for example, hydrazine, formaldehyde, sodium formate, $NaBH_4$ at temperatures between 0° C. and 200° C. or gaseous hydrogen at temperatures between 0° C. and 500° C., preferably between 20 and 300° C., particularly preferably 30–250° C., and reaction of the platinum metal with hydrogen halide or gaseous halogen at temperatures between 20° C. and 600° C., preferably between 50 and 500° C.

During the application of platinum metal and cocatalyst to the support, the mixture can be stirred. However, it can also be advantageous to allow the mixture to stand or to shake it, so that shaped bodies, if used, are not damaged by a stirrer. After application of platinum metal and cocatalyst to the support, the supported catalyst is separated off, for example, by filtration, sedimentation or centrifugation. In a further embodiment of the invention, the solvent is separated off by distillation.

After separating off the solvent, the supported catalysts thus obtained are dried. This can be carried out in air, in vacuo or in a stream of gas. Suitable gases for drying the supported catalyst in a stream of gas are nitrogen, oxygen, carbon monoxide, carbon dioxide and noble gases and also any mixtures of the gases specified, preferably, for example, air. Likewise suitable are gaseous hydrocarbons such as alkanes (e.g. methane, ethane, propane), alkenes such as ethene, propene, butene, butadiene and alkines such as ethine, propine, etc, in any composition. Drying is carried out at from 20 to 200° C., preferably at from 40 to 180° C., particularly preferably at from 60 to 150° C. The drying time depends, for example, on the porosity of the support used and on the solvent used. It is generally a few hours, for example from 0.5 to 50 hours, preferably from 1 to 40 hours, particularly preferably from 1 to 30 hours.

After drying, the dried supported catalysts can be calcined. This can be carried out in air, in vacuo or in a stream of gas. Suitable gases for calcination of the supported catalyst in a stream of gas are, for example, nitrogen, oxygen, carbon dioxide or noble gases and also any mixtures of the gases specified, preferably, for example, air. Calcination is carried out at from 100 to 800° C., preferably from 100 to 700° C., particularly preferably at from 100 to 600° C. It may here be advantageous if the composition of the gas is changed abruptly or continuously during the calcination. An abrupt change of the calcination gas composition can be carried out, for example, by after 10 hours increasing the $O_2$ content from 10% by volume to 20% by volume for the remaining 10 hours and maintaining the temperature. A continuous change of the calcination gas composition can be carried out, for example, by maintaining the temperature and increasing the oxygen content from 0% by volume to 20% by volume over 20 hours at a rate of 1% by volume/h. The calcination time is generally a few hours, for example from 0.5 to 50 hours, preferably from 1 to 40 hours, particularly preferably from 1 to 30 hours.

The aromatic hydroxy compounds which can be reacted using the supported catalysts of the invention are, for example, phenol, o-, m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphenol, 1-naphthol, 2-naphthol and bisphenol A, preferably phenol. If the aromatic hydroxy compound is substituted, there are generally 1 or 2 substituents which are $C_1$–$C_4$-alkyl, $C_1$–$C_4$-alkoxy, fluorine, chlorine or bromine.

For the process of the invention, any organic or inorganic bases or mixtures thereof can be used. Examples of inorganic bases which may be mentioned are, without restricting the process of the invention, alkali metal hydroxides and carbonates, carboxylates or other salts of weak acids and also alkali metal salts of aromatic hydroxy compounds of the formula (II), e.g. alkali metal phenoxides. Of course, it is also possible to use the hydrates of alkali metal phenoxides in the process of the invention. An example of such a hydrate which may be mentioned here, without restricting the process of the invention, is sodium phenoxide trihydrate. However, the amount of water added is preferably such that a maximum of 5 mol of water are used per mol of base. Higher water concentrations lead, in general to poorer conversions and decomposition of the carbonates formed. Organic bases which may be mentioned, without restricting the process of the invention, are tertiary amines which can bear $C_6$–$C_{10}$-aryl, $C_7$–$C_{12}$-aralkyl and/or $C_1$–$C_{20}$-alkyl radicals as organic radicals or are pyridine bases or hydrogenated pyridine bases, for example triethylamine, tripropylamine, tributylamine, trioctylamine, benzyldimethylamine, dioctylbenzylamine, dimethylphenethylamine, 1-dimethylamino-2-phenylpropane, pyridine, N-methylpiperidine, 1,2,2,6,6-pentamethylpiperidine. The base used is preferably an alkali metal salt of an aromatic hydroxy compound, particularly preferably an alkali metal salt of the aromatic hydroxy compound (II) which is also to be reacted to form the organic carbonate. These alkali metal salts can be lithium, sodium, potassium, rubidium or caesium salts. Preference is given to using lithium, sodium and potassium phenoxide, particularly preferably sodium phenoxide.

The base can be added to the reaction mixture as a pure compound in solid form or as a melt. In a further embodiment of the invention, the base is added to the reaction mixture as a solution containing from 0.1 to 80% by weight, preferably from 0.5 to 65% by weight, particularly preferably from 1 to 50% by weight, of the base. Solvents which can be used here are alcohols or phenols, such as the phenol (II) to be reacted, or inert solvents. Examples which may be mentioned are those mentioned further below as reaction media. These solvents can be used alone or in any combination with one another. Thus, one embodiment of the process of the invention comprises, for example, dissolving the base in a phenol melt which has been diluted with a solvent. The base is preferably dissolved in the melt of an aromatic hydroxy compound, particularly preferably in a melt of the aromatic hydroxy compound (II) which is to be reacted to form the organic carbonate. Very particularly preferably, the base is added in solution in phenol.

The base is added in an amount which is independent of the stoichiometry. The ratio of the platinum metal, e.g. palladium, to the base is preferably selected such that from 0.1 to 500, preferably from 0.3 to 200, particularly preferably from 0.9 to 130, equivalents of base are used per mol of platinum metal, e.g. palladium.

The process of the invention is preferably carried out without solvent. Of course, inert solvents can also be used. Examples of solvents which may be mentioned are dimethylacetamide, N-methylpyrrolidinone, dioxane, t-butanol, cumyl alcohol, isoamyl alcohol, tetramethylurea, diethylene glycol, halogenated hydrocarbons (e.g. chlorobenzene or dichlorobenzene) and ethers.

The quaternary salts used for the purposes of the present invention can be, for example, ammonium or phosphonium salts substituted by organic radicals. Suitable salts for use in the process of the invention are ammonium and phosphonium salts which bear $C_6$–$C_{10}$-aryl, $C_7$–$C_{12}$-aralkyl and/or $C_1$–$C_{20}$-alkyl radicals as organic radicals and a halide, tetrafluoroborate or hexafluorophosphate as anion. In the process of the invention, preference is given to ammonium salts which bear $C_6$–$C_{10}$-aryl, $C_7$–$C_{12}$-aralkyl and/or $C_1$–$C_{20}$-alkyl radicals as organic radicals and a halide as anion, particular preference being given to tetrabutylammonium bromide. The amount of such a quaternary salt is from 0.1 to 50% by weight, based on the weight of the reaction mixture. This amount is preferably from 0.5 to 15% by weight, particular preferably from 1 to 5% by weight.

The process of the invention is, preferably without solvent, carried out at from 30 to 200° C., preferably at from 30 to 150° C., particularly preferably at from 40 to 120° C., and at a pressure of from 1 to 150 bar, preferably from 2 to 50 bar, particularly preferably at from 5 to 25 bar.

The supported catalysts can be used as powders or shaped bodies and can be separated again from the reaction mixture, for example by filtration, sedimentation or centrifugation.

The preparation of aromatic carbonates using the supported catalysts of the invention can be performed by means of different process variants. One possibility is a batchwise procedure. In the case of a continuous procedure in countercurrent or cocurrent or in the downflow mode over a fixed bed catalyst, space velocities of from 0.01 to 20 g of aromatic hydroxy compound per gram of supported catalyst and hour, preferably from 0.05 to 10 g of aromatic hydroxy compound per gram of supported catalyst and hour, particularly preferably from 0.1 to 5 g of aromatic hydroxy compound per gram of supported catalyst and hour, are set. The supported catalysts used in batchwise experiments can be repeatedly used for identical starting materials without purification. In the case of a continuous procedure, the supported catalysts used can remain in the reactor for a long time.

Preferably, the supported catalysts of the invention are used in a continuous procedure in a single reactor or in a cascade of reactors.

If the supported catalyst is used as a powder, the stirred vessels to be used are fitted with stirrers suitable for mixing the reaction components. When working with supported catalyst powders in suspension in stirred vessels or bubble columns, amounts of from 0.001 to 50% by weight, preferably from 0.01 to 20% by weight, particularly preferably from 0.1 to 10% by weight, of supported catalyst powder are used, based on the amount of aromatic hydroxy compound used. In particularly preferred embodiments, the heterogeneous supported catalyst is used as a shaped body in a fixed position in stirred vessels, bubble columns, downflow reactors or cascades of these reactors; in this context, the various types of reactor may also occur simultaneously in one cascade.

EXAMPLES

Example 1 a) Application of Palladium and Manganese to a Pulverulent Titanium Dioxide:

300 ml of a solution of 40.5 g (0.16 mol) of manganese(II) nitrate tetrahydrate in water were added at room temperature to a slurry of 283.5 g of titanium dioxide powder (Norton) in 1500 ml of water. The slurry was then made alkaline using dilute sodium hydroxide solution. The resulting suspension was filtered with suction, washed with water, dried at 100° C. and heat treated at 300° C. for 3 hours. The manganese-doped support was slurried in 1500 ml of water and admixed with 300 ml of a solution containing 50 g of sodium tetrachloropalladate(II) solution containing 15% of palladium. The slurry was then made alkaline using dilute sodium hydroxide solution. The suspension obtained was filtered with suction, washed and dried at 100° C. The catalyst contained 2.5% by weight of Pd and 3% by weight of Mn, in each case calculated as metal.

b) Use of the Supported Catalyst for Preparing Diphenyl Carbonate:

In an autoclave (1 l) fitted with gas-introduction stirrer, condenser and downstream cold trap, 8.31 g of tetrabutylammonium bromide were dissolved in 450 g of phenol at 80° C. 4 g of the above-described supported catalyst and 2.21 g of sodium phenoxide dissolved in 50 g of phenol were then added. The pressure was then set to 10 bar while passing in a gas mixture of carbon monoxide and oxygen (95:5% by volume). The amount of gas mixture was set to 300 standard l/h. Every hour, a sample was taken from the reaction mixture and analysed by gas chromatography. The analyses indicated that the reaction mixture contained 8.1% of diphenyl carbonate after one hour, 14.3% of diphenyl carbonate after 2 hours and 18.6% of diphenyl carbonate after 3 hours. 14.1 g of a phenol/water mixture had condensed in the cold trap.

c) A Further catalyst sample from Example 1a) was used under the same reaction conditions, except that a homogeneously dissolved cocatalyst, namely 0.77 g of manganese acetylacetonate, was additionally present. Every hour, a sample was taken from the reaction mixture and analysed by gas chromatography. The analyses indicated that the reaction mixture contained 8.3% of diphenyl carbonate after one hour, 14.5% of diphenyl carbonate after 2 hours and 18.5% of diphenyl carbonate after 3 hours. 13.9 g of a phenol/water mixture had condensed in the cold trap. The presence of a homogeneously dissolved cocatalyst does not give a better result and is thus no longer necessary according to the invention.

Example 2 a) Application of Palladium and Cobalt to a Pulverulent Titanium Dioxide:

283.5 g of titanium dioxide powder (Norton) were added at room temperature to a solution of 18.75 g of palladium(II) bromide (0.07 mol), 28.5 g of sodium bromide (0.28 mol) and 33.4 g of cobalt(II) bromide (0.15 mol) in 1500 ml of water. The mixture was then made alkaline using dilute sodium hydroxide solution. The suspension was filtered with suction, washed and dried at 100° C. The catalyst contained 2.5% by weight of Pd and 3% by weight of Co, in each case calculated as metal.

b) Use of the Supported Catalyst for Preparing Diphenyl Carbonate:

The use of the supported catalyst for preparing diphenyl carbonate was carried out as in Example 1. The analyses indicated that the reaction mixture contained 6.1% of diphenyl carbonate after one hour, 11.3% of diphenyl carbonate after 2 hours and 15.0% of diphenyl carbonate after 3 hours. 11.5 g of a phenol/water mixture had condensed in the cold trap.

Example 3 a) Application of Palladium and Manganese to a Titanium Dioxide Extrudate:

200 ml of titanium dioxide extrudate were impregnated with 58.4 ml of a solution of 21.6 g of manganese(II) chloride in water. The extrudates were then dried at 110° C. under nitrogen. The manganese-doped support was impregnated with 58 ml of an aqueous solution containing 33.3 g of sodium tetrachloropalladate(II) solution containing 15% of palladium. The extrudates were then dried at 110° C. under nitrogen. The finished catalyst contained 25 g of Pd per litre and 30 g of Mn per litre, in each case calculated as metal.

b) Use of the Supported Catalyst for Preparing Diphenyl Carbonate:

The use of the supported catalyst for preparing diphenyl carbonate was carried out as in Example 1, except that the catalyst was fixed in position in a wire mesh basket. The analyses indicated that the reaction mixture contained 4.6% of diphenyl carbonate after one hour, 8.7% of diphenyl carbonate after 2 hours and 11.6% of diphenyl carbonate after 3 hours. 9.2 g of a phenol/water mixture had condensed in the cold trap.

Example 4 a) Application of Rhodium and Manganese to a Titanium Dioxide Extrudate:

200 ml of titanium dioxide extrudate were impregnated with 58.4 ml of a solution of 21.6 g of manganese(II) chloride in water. The extrudates were then dried at 110° C. under nitrogen. The manganese-doped support was impregnated with 58 ml of an aqueous solution containing 12.94 g of rhodium(III) chloride hydrate. The extrudates were then dried at 110° C. under nitrogen. The catalyst contained 25 g of rhodium per litre and 30 g of Mn per litre, in each case calculated as metal.

b) Use of the Supported Catalyst for Preparing Diphenyl Carbonate:

The use of the supported catalyst for preparing diphenyl carbonate was carried out as in Example 3. The analyses indicated that the reaction mixture contained 1.4% of diphenyl carbonate after one hour, 2.9% of diphenyl carbonate after 2 hours and 4.1% of diphenyl carbonate after 3 hours. 3.5 g of a phenol/water mixture had condensed in the cold trap.

Example 5 a) Application of Palladium and Manganese to a Pulverulent Titanium Dioxide:

274.5 g of titanium dioxide powder (Norton) were added at room temperature to a solution of 82.8 g of manganese(II) acetylacetonate (0.33 mol) in 750 ml of ethanol. The mixture was then made alkaline using dilute sodium phenoxide solution, The resulting suspension was filtered with suction and washed. The manganese-doped support was slurried in 1500 ml of water and admixed with 600 ml of an aqueous solution containing 50 g of sodium tetrachloropalladate(II) solution containing 15% of Pd. The mixture was then made alkaline using dilute sodium phenoxide solution. The suspension obtained was filtered with suction, washed and dried at 100° C. The catalyst contained 2.5% by weight of Pd and 6% by weight of Mn, in each case calculated as metal.

b) Use of the Supported Catalyst for Preparing Diphenyl Carbonate:

The use of the supported catalyst for preparing diphenyl carbonate was carried out as in Example 1. The analyses indicated that the reaction mixture contained 8.6% of diphenyl carbonate after one hour, 15.2% of diphenyl carbonate after 2 hours and 18.2% of diphenyl carbonate after 3 hours. 15.0 g of a phenol/water mixture had condensed in the cold trap.

Example 6 a) Application of Palladium, Copper and Molybdenum to a Titanium Dioxide Extrudate:

200 ml of titanium dioxide extrudate were pre-impregnated with 100 ml of 25% strength aqueous ammonia solution. Subsequently, the support was treated with a solution comprising 300 ml of 25% strength aqueous ammonia solution, 1.44 g of palladium(II) chloride (0.008 mol), 2.76 g of copper(II) chloride dihydrate (0.016 mol) and 3.04 g of ammonium molybdate(VI) tetrahydrate (0.0025 mol). The mixture was tumbled for 1 hour at 80° C. and the volatile constituents were subsequently taken off in vacuo at 80° C. After drying under nitrogen at 200° C., a catalyst containing 4.3 g of Pd, 5.2 g of Cu and 8.3 g of Mo per litre of catalyst composition was obtained.

b) Use of the Supported Catalyst for Preparing Diphenyl Carbonate:

The use of the supported catalyst for preparing diphenyl carbonate was carried out as in Example 3. The analyses indicated that the reaction mixture contained 2.2% of diphenyl carbonate after one hour, 4.5% of diphenyl carbonate after 2 hours and 6.3% of diphenyl carbonate after 3 hours. 5.7 g of a phenol/water mixture had condensed in the cold trap.

Example 7 a) Application of Palladium and Vanadium to a Pulverulent Lanthanum Oxide 189 g of lanthanum(III) oxide powder (Bayer) were added at 70° C. to a solution of 13.8 g of ammonium vanadate (0.12 mol) in 1380 ml of $H_2O$ acidified with $HNO_3$. The suspension was then filtered with suction, dried and heat treated for 4 hours at 400° C. The vanadium-doped support was added at room temperature to a solution of 12.5 g of palladium(II) bromide (0.05 mol) and 19 g of sodium bromide (0.18 mol) in 1000 ml of $H_2O$. The suspension was stirred, filtered with suction, washed and dried at 60° C.

b) Use of the Supported Catalyst for Preparing Diphenyl Carbonate

The use of the supported catalyst for preparing diphenyl carbonate was carried out as in Example 1. The analyses indicated that the reaction mixture contained 2.0% of diphenyl carbonate after one hour, 3.6% of diphenyl carbonate after 2 hours and 4.7% of diphenyl carbonate after 3 hours. 3.5 g of a phenol/water mixture had condensed in the cold trap.

Example 8 a) Application of Palladium and Manganese to a Pulverulent Iron Oxide 200 ml of a solution of 21.6 g of manganese(II) chloride tetrahydrate (0.11 mol) in $H_2O$ were added at room temperature to a slurry of 189 g of iron(III) oxide (Bayer) in 1000 ml of $H_2O$. The slurry was then made alkaline using dilute sodium hydroxide solution. The suspension was admixed with 300 ml of a solution of 12.5 g of palladium(II) bromide (0.05 mol) and 19 g of sodium bromide (0.18 mol) in $H_2O$. The mixture was then made alkaline using dilute sodium hydroxide solution. The suspension was filtered with suction, washed and dried at 100° C.

b) Use of the Supported Catalyst for Preparing Diphenyl Carbonate

The use of the supported catalyst for preparing diphenyl carbonate was carried out as in Example 1. The analyses indicated that the reaction mixture contained 2.9% of diphenyl carbonate after one hour, 5.1% of diphenyl carbonate after 2 hours and 6.7% of diphenyl carbonate after 3 hours. 5.1 g of a phenol/water mixture had condensed in the cold trap.

Example 9 a) Application of Palladium and Manganese to a Pulverulent Magnesium Oxide 200 ml of a solution of 21.6 g of manganese(II) chloride tetrahydrate (0.11 mol) in $H_2O$ and 300 ml of a solution of 12.5 g of palladium(II) bromide (0.05 mol) and 19 g of sodium bromide (0.18 mol) in $H_2O$ were added at room temperature to a slurry of 189 g of magnesium(II) oxide (Bayer) in 1000 ml of $H_2O$. The suspension was stirred, washed and dried at 100° C.

b) Use of the Supported Catalyst for Preparing Diphenyl Carbonate

The use of the supported catalyst for preparing diphenyl carbonate was carried out as in Example 1. The analyses indicated that the reaction mixture contained 1.5% of diphenyl carbonate after one hour, 2.6% of diphenyl carbonate after 2 hours and 3.3% of diphenyl carbonate after 3 hours. 2.5 g of a phenol/water mixture had condensed in the cold trap.

Example 10 a) Application of Palladium and Manganese to a Pulverulent Activated Carbon 200 ml of a solution of 21.6 g of manganese(II) chloride tetrahydrate (0.11 mol) in $H_2O$ and 300 ml of a solution of 12.5 g of palladium(II) bromide (0.05 mol) and 19 g of sodium, bromide (0.18 mol) in $H_2O$ were added at room temperature to a slurry of 189 g of activated carbon (Norit) in 1000 ml of $H_2O$. The suspension was stirred, filtered with suction, washed and dried at 100° C.

b) Use of the Supported Catalyst for Preparing Diphenyl Carbonate

The use of the supported catalyst for preparing diphenyl carbonate was carried out as in Example 1. The analyses indicated that the reaction mixture contained 5.2% of diphenyl carbonate after one hour, 9.2% of diphenyl carbonate after 2 hours and 11.9% of diphenyl carbonate after 3 hours. 9.0 g of a phenol/water mixture had condensed in the cold trap.

Example 11 a) Application of Palladium and Manganese to a Pulverulent Silicon Oxide 189 g of silicon dioxide (Tolsa) were added to a solution of 27.7 g of manganese(II) acetylacetonate (0.11 mol) and 33.3 g of sodium tetrachloropalladate(II) solution containing 15% of Pd in ethanol. The mixture was then made alkaline using dilute sodium hydroxide solution. The suspension was stirred, filtered with suction, washed and dried at 100° C.

b) Use of the Supported Catalyst for Preparing Diphenyl Carbonate

The use of the supported catalyst for preparing diphenyl carbonate was carried out as in Example 1. The analyses indicated that the reaction mixture contained 8.1% of diphenyl carbonate after one hour, 14.3% of diphenyl carbonate after 2 hours and 18.6% of diphenyl carbonate after 3 hours. 14.1 g of a phenol/water mixture had condensed in the cold trap.

Example 12 a) Application of Palladium and Manganese to a Pulverulent Aluminium Oxide 189 g of aluminium(III) oxide (Rhone Poulenc) were added to a solution of 27.7 g of manganese(II) acetylacetonate (0.11 mol) and 33.3 g of sodium tetrachloropalladate(II) solution containing 15% of Pd in ethanol. The mixture was then made alkaline using dilute sodium hydroxide solution. The suspension was stirred, filtered with suction, washed and dried at 100° C.

b) Use of the Supported Catalyst for Preparing Diphenyl Carbonate

The use of the supported catalyst for preparing diphenyl carbonate was carried out as in Example 1. The analyses indicated that the reaction mixture contained 5.8% of diphenyl carbonate after one hour, 10.2% of diphenyl carbonate after 2 hours and 13.2% of diphenyl carbonate after 3 hours. 10.0 g of a phenol/water mixture had condensed in the cold trap.

Example 13 a) Application of Palladium and Manganese to a Pulverulent Manganese Oxide 189 g of manganese(IV) oxide (Fluka) were added to a solution of 27.7 g of manganese(II) acetylacetonate (0.11 mol) and 10.4 g of palladium(II) acetate (0.05 mol) in ethanol. The suspension was evaporated on a rotary evaporator.

b) Use of the Supported Catalyst for Preparing Diphenyl Carbonate

The use of the supported catalyst for preparing diphenyl carbonate was carried out as in Example 1. The analyses indicated that the reaction mixture contained 3.7% of diphenyl carbonate after one hour, 6.6% of diphenyl carbonate after 2 hours and 8.6% of diphenyl carbonate after 3 hours. 6.5 g of a phenol/water mixture had condensed in the cold trap.

Example 14 a) Application of Palladium and Cobalt to a Pulverulent Manganese Oxide 189 g of manganese(IV) oxide (Fluka) were added to a solution of 12.5 g of palladium(II) bromide (0.05 mol), 24.2 g of cobalt(II) chloride hexahydrate (0.1 mol) and 19 g of sodium bromide (0.18 mol) in $H_2O$. The suspension was stirred, made alkaline using sodium hydroxide solution, filtered with suction, washed and dried at 100° C.

b) Use of the Supported Catalyst for Preparing Diphenyl Carbonate

The use of the supported catalyst for preparing diphenyl carbonate was carried out as in Example 1. The analyses indicated that the reaction mixture contained 3.5% of diphenyl carbonate after one hour, 6.1% of diphenyl carbonate after 2 hours and 8.0% of diphenyl carbonate after 3 hours. 6.1 g of a phenol/water mixture had condensed in the cold trap.

Example 15 a) Application of Palladium and Manganese to Activated Carbon Extrudates 200 ml of activated carbon extrudates (Norit) were impregnated with 58 ml of impregnation liquid containing 21.6 g of manganese(II) chloride tetrahydrate (0.11 mol) and 33.3 g of sodium tetrachloropalladate(II) solution containing 15% of Pd in $H_2O$. The extrudates were then dried under nitrogen.

b) Use of the Supported Catalyst for Preparing Diphenyl Carbonate

The use of the supported catalyst for preparing diphenyl carbonate was carried out as in Example 1, except that the catalyst was fixed in position in a wire mesh basket. The analyses indicated that the reaction mixture contained 3.2% of diphenyl carbonate after one hour, 5.6% of diphenyl carbonate after 2 hours and 7.3% of diphenyl carbonate after 3 hours. 5.5 g of a phenol/water mixture had condensed in the cold trap.

Example 16 a) Application of Palladium and Manganese to a Pulverulent Montmorillonite 189 g of montmorillonite (Fluka) were added to a solution of 27.7 g of manganese(II) acetylacetonate (0.11 mol) in ethanol. The mixture was then made alkaline using dilute sodium hydroxide solution. The suspension was filtered with suction and washed. The manganese-doped support was slurried in 1000 ml of $H_2O$ and admixed with 33.3 g of sodium tetrachloropalladate(II) solution containing 15% of Pd. The suspension was filtered with suction and dried at 100° C.

b) Use of the Supported Catalyst for Preparing Diphenyl Carbonate

The use of the supported catalyst for preparing diphenyl carbonate was carried out as in Example 1. The analyses indicated that the reaction mixture contained 3.4% of diphenyl carbonate after one hour, 6.0% of diphenyl carbonate after 2 hours and 7.8% of diphenyl carbonate after 3 hours. 5.9 g of a phenol/water mixture had condensed in the cold trap.

What is claimed is:

1. A supported catalyst containing, in the reaction-ready state, (i) a platinum metal, a platinum metal halide or a complex containing a platinum metal halide, or a compound which can be converted under the reaction conditions into a platinum metal, a platinum metal halide or a complex containing a platinum metal halide, in an amount of 0.01–15% by weight, calculated as platinum metal and based on the total weight of the catalyst, and (ii) a metal compound acting as cocatalyst from groups IB, IIB, IIIA, IIIB, IVA, IVB, VB, VIB, VIIB, the iron group (atomic numbers 26–28) or the rare earth metals (atomic numbers 58–71) of the Periodic Table of the Elements (Mendeleev) in an amount of 0.01–15% by weight, calculated as metal and based on the total weight of the catalyst.

2. The catalyst of claim 1, containing the platinum metal, the platinum metal halide or a complex containing the platinum metal halide, or a compound which can be converted into the platinum metal, the platinum metal halide or a complex containing the platinum metal halide, in an amount of 0.05–10% by weight, calculated as platinum metal and based on the total weight of the catalyst.

3. The catalyst of claim 1, containing the metal compound acting as a cocatalyst in an amount of 0.05–10% by weight, calculated as metal and based on the total weight of the catalyst.

4. The catalyst of claim 1, wherein the platinum metal present is Pd or Rh, as metal, metal halide or a complex containing metal halide.

5. The catalyst of claim 4, wherein the platinum metal present is Pd.

6. The catalyst of claim 1, wherein the cocatalytic metal compound present is a compound of a metal from the group of Mn, Cu, Co, V, Zn, Ce and Mo.

7. The catalyst of claim 6, wherein the cocatalytic metal compound present is a compound of a metal from the group of Mn, Cu, Co, Ce and Mo.

8. The catalyst of claim 1 which can be prepared by joint or successive application of a platinum metal compound and a compound acting as cocatalyst to a support, wherein the platinum metal compound used is a platinum metal halide or a platinum metal halide complex or a compound which can be converted under the reaction conditions into a platinum metal, a platinum metal halide or a complex containing a platinum metal halide, or the platinum metal halide or the platinum metal halide complex is formed on the catalyst support from a halide-free platinum metal compound and a halide-containing compound or is formed on the catalyst support from a halide-free platinum metal compound by reaction with a reducing agent at 0–500° C. to first give the elemental platinum metal which is subsequently further reacted with gaseous hydrogen halide or gaseous halogen at 20–600° C.

9. The catalyst of claim 8, wherein platinum metal halides or complexes containing platinum metal halides and nitriles, CO, olefins, amines, phosphines, water or further halide are used or are produced on the support by joint or successive application of a platinum metal compound from the group of acetates, nitrates, acetylacetonates, oxalates and hydroxides and a halogen-containing compound from the group NaCl, NaBr, $MgCl_2$, $MgBr_2$, $MnCl_2$, $MnBr_2$, $CuCl_2$ and tetrabutylammonium bromide.

10. The catalyst of claim 8, wherein the compound acting as cocatalyst is applied using a halide, oxide, carboxylate of a $C_2$–$C_6$-carboxylic acid, diketonate, nitrate or a complex, which can contain CO, olefins, amines, nitriles, phosphines or halide, of a metal acting as cocatalyst.

11. In the preparation of an aromatic carbonate of the formula

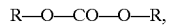

where

R is substituted or unsubstituted $C_6$–$C_{12}$-aryl, by reaction of an aromatic hydroxy compound of the formula

where

R is as defined above, with carbon monoxide and oxygen in the presence of a quaternary ammonium or phosphonium salt and a base at 30–200° C. and at a pressure of 1–150 bar, and in the presence of a catalyst, the improvement wherein the catalyst comprises a supported catalyst according to claim 1.

12. The process of claim 11, wherein the supported catalyst is, in a continuous procedure in countercurrent or cocurrent, or using the catalyst in a fixed position in a stirred vessel, bubble column reactor or in the downflow mode over a fixed-bed catalyst, exposed to from 0.01 to 20 g of aromatic hydroxy compound per gram of supported catalyst and hour, and when working in suspension in stirred vessels or bubble columns, the supported catalyst is used in an amount of from 0.001 to 50% by weight, based on the amount of aromatic hydroxy compound used.

13. The process of claim 11, wherein the base used is a tertiary amine, alkali metal phenoxide or alkali metal salt of a weak acid.

14. The process of claim 11, wherein the quaternary salt used is a tetraalkylammonium or tetraalkylphosphonium salt.

15. The process of claim 12, wherein the catalyst, when in the form of a fixed-bed catalyst, is exposed to from 0.05 to 10 g of aromatic hydroxy compound per gram of catalyst and hour.

16. The process of claim 15, wherein the catalyst, when in the form of a fixed-bed catalyst, is exposed to from 0.1 to 5 gram of aromatic hydroxy compound per gram of catalyst and hour.

17. The process of claim 12, wherein the catalyst, when in suspended form, is used in an amount of from 0.01 to 20% by weight, based on the amount of aromatic compound used.

18. The process of claim 17, wherein the catalyst, when in suspended form, is used in an amount of from 0.1 to 10% by weight, based on the amount of aromatic compound used.

19. The process of claim 11, which is carried out at 30–150° C.

20. The process of claim 11, which is carried out at 2–50 bar.

* * * * *